US008398949B2

United States Patent
Meyer et al.

(10) Patent No.: US 8,398,949 B2
(45) Date of Patent: Mar. 19, 2013

(54) CARBON NANOTUBE POWDER, CARBON NANOTUBES, AND PROCESSES FOR THEIR PRODUCTION

(75) Inventors: Helmut Meyer, Odenthal (DE); Heiko Hocke, Leverkusen (DE); Ralph Weber, Leichlingen (DE); Martin Schmid, Kürten (DE); Elmar Bramer-Weger, Alfter (DE); Matthias Voetz, Leverkusen (DE); Leslaw Mleczko, Dormagen (DE); Reiner Rudolf, Leverkusen (DE); Aurel Wolf, Wülfrath (DE); Sigurd Buchholz, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 401 days.

(21) Appl. No.: 12/208,468

(22) Filed: Sep. 11, 2008

(65) Prior Publication Data

US 2009/0124705 A1    May 14, 2009

(30) Foreign Application Priority Data

Sep. 14, 2007    (DE) .......................... 10 2007 044 031

(51) Int. Cl.
*D01F 9/12* (2006.01)
*D01F 9/127* (2006.01)

(52) U.S. Cl. ............... 423/447.2; 423/447.1; 423/447.3; 977/742; 977/743; 977/843

(58) Field of Classification Search .... 423/447.1–447.3; 977/742–754, 842–848; 428/367
See application file for complete search history.

(56) References Cited

U.S. PATENT DOCUMENTS

| 5,413,866 | A  | * | 5/1995 | Baker et al. ................. 423/447.2 |
| 6,426,134 | B1 | * | 7/2002 | Lavin et al. ................. 428/300.1 |
| 2004/0151654 | A1 | * | 8/2004 | Wei et al. ................... 423/447.3 |

FOREIGN PATENT DOCUMENTS

| CA | 2 374 848 A1 | 9/2003 |
| EP | 56004 | 7/1982 |
| EP | 0 205 556 | 6/1986 |
| EP | 1 399 384 A2 | 1/2003 |
| GB | 1 469 930 | 4/1977 |
| WO | 2007 09337 A1 | 1/2007 |

OTHER PUBLICATIONS

Baughman, et al., Carbon Nanotubes-the Route Toward Applications, Science 2002; 787-792.*
Dravid, et al., Buckytubes and Derivatives: Their Growth and Implications for Buckyball Formation, Science 1993; 259: 1601-1604.*
Ebbesen, et al., Large-scale synthesis of carbon nanotubes, Nature 1992; 358: 220-222.*
Levenspiel, Chemical Reaction Engineering, 93 (3d ed., John Wiley & Sons 1999).*

(Continued)

*Primary Examiner* — Daniel C. McCracken
(74) *Attorney, Agent, or Firm* — Norris McLaughlin & Marcus PA

(57) ABSTRACT

A novel carbon nanotube powder containing carbon nanotubes which have a roll-like structure, also novel carbon nanotubes having a roll-like structure, novel processes for the production of the carbon nanotube powders and of the carbon nanotubes, and their use as an additive or substrate for various applications are described.

14 Claims, 2 Drawing Sheets

OTHER PUBLICATIONS

Bursill, et al., Cross-sectional high-resolution transmission electron microscopy study of the structures of carbon nanotubes, Philosophical Magazine A 1995; 71(5): 1161-1176.*

Mordkovich, et al., Intercalation into carbon nanotubes, Carbon 1996; 34: 1301-1303.*

Bacon, Growth, Structure, and Properties of Graphite Whiskers, J. Appl. Phys. 1960; 31(2): 283-290.*

Braga, et al., Structure and Dynamics of Carbon Nanoscrolls, Nano Letters 2004; 4(5): 881-884.*

Bursill, Cross-sectional high-resolution transmission electron microscopy study o fhte structures of carbon nanotubes, Philosophical Magazine A 1995; 71: 1161-1176.*

Reznik, et al., X-ray powder diffraction from carbon nanotubes and nanoparticles, Physical Review B 1995; 52: 116-124.*

Shioyama, et al, A new route to carbon nanotubes, Carbon 2003; 41: 179-181.*

* cited by examiner

CARBON NANOTUBE POWDER, CARBON NANOTUBES, AND PROCESSES FOR THEIR PRODUCTION

The invention relates to a novel carbon nanotube powder containing carbon nanotubes having a roll-like structure, to novel carbon nanotubes having a roll-like structure, to novel processes for the production of the carbon nanotube powder and of the carbon nanotubes, and to the use thereof. The carbon nanotubes are referred to hereinbelow as "CNTs" for short.

BACKGROUND OF THE INVENTION

According to the prior art, carbon nanotubes are understood as being mainly cylindrical carbon tubes having a diameter of from 3 to 100 nm and a length that is a multiple of the diameter. These tubes consist of one or more layers of ordered carbon atoms and have a core that differs in terms of morphology. These carbon nanotubes are also referred to as "carbon fibrils" or "hollow carbon fibers", for example.

Carbon nanotubes have been known for a long time in the specialist literature. Although Iijima (publication: S. Iijima, Nature 354, 56-58, 1991) is generally considered to have discovered nanotubes, such materials, in particular fibrous graphite materials having a plurality of graphite layers, have been known since the 1970s or early 1980s. The deposition of very fine fibrous carbon from the catalytic decomposition of hydrocarbons was described for the first time by Tates and Baker (GB 1469930 A1, 1977 and EP 56004 A2, 1982). However, the carbon filaments produced on the basis of short-chained hydrocarbons are not described in greater detail in respect of their diameter.

The production of carbon nanotubes having diameters of less than 100 nm was described for the first time in EP 205 556 B1 or WO A 86/03455. In this case, the production is carried out using light (i.e. short- and medium-chained aliphatic or mono- or bi-nuclear aromatic) hydrocarbons and an iron-based catalyst, on which carbon carrier compounds are decomposed at a temperature above 800 to 900° C.

The methods known today for the production of carbon nanotubes include arc discharge, laser ablation and catalytic processes. In many of these processes, carbon black, amorphous carbon and fibers having large diameters are formed as by-products. In the case of the catalytic processes, a distinction can be made between deposition on supported catalyst particles and deposition on metal centers formed in situ and having diameters in the nanometer range (so-called flow processes). In the case of production by the catalytic deposition of carbon from hydrocarbons that are gaseous under reaction conditions (CCVD; catalytic carbon vapor deposition hereinbelow), acetylene, methane, ethane, ethylene, butane, butene, butadiene, benzene and further carbon-containing starting materials are mentioned as possible carbon donors.

The catalysts generally contain metals, metal oxides or decomposable or reducible metal components. For example, Fe, Mo, Ni, V, Mn, Sn, Co, Cu and others are mentioned as metals in the prior art. Although most of the individual metals have a tendency to form nanotubes, high yields and low amorphous carbon contents are advantageously achieved according to the prior art with metal catalysts that contain a combination of the above-mentioned metals.

According to the prior art, particularly advantageous systems are based on combinations that contain Fe or Ni. The formation of carbon nanotubes and the properties of the tubes that are formed are dependent in a complex manner on the metal component, or combination of a plurality of metal components, used as catalyst, the support material used and the interaction between the catalyst and the support, the starting material gas and partial pressure, the admixture of hydrogen or further gases, the reaction temperature and the dwell time or the reactor used. An optimization represents a particular challenge for a technical process.

It is to be noted that the metal component used in the CCVD and referred to as the catalyst is consumed in the course of the synthesis process. This consumption is attributable to a deactivation of the metal component, for example owing to the deposition of carbon on the entire particle, which results in complete coverage of the particle (this is known to the person skilled in the art as "encapping"). Reactivation is generally not possible or is not economically expedient. In many cases, a maximum of only a few grams of carbon nanotubes per gram of catalyst are obtained, the catalyst here comprising the totality of the support and the catalyst used. On account of the described consumption of catalyst, a high yield of carbon nanotubes, based on the catalyst used, is a fundamental requirement of the catalyst and the process.

For the industrial production of carbon nanotubes, for example as a constituent for improving the mechanical properties or conductivity of composite materials, it is desirable, as in all industrial processes, to have a high space-time yield while retaining the particular properties of the nanotubes and minimizing the energy and fuel that are to be used. Applications based on the laser ablation of carbon often yield only low production rates and high contents of amorphous carbon or carbon black. In most cases, such systems on the laboratory scale, with production rates of a few grams per day, can be converted to an industrial scale only with difficulty. Laser ablation is also expensive and a scale-up is difficult. Although various processes described in the literature for the production of carbon nanotubes by CCVD show the suitability of various catalysts in principle, they often exhibit only low productivity, however.

Various processes and catalysts are known in the patent literature for the production of carbon nanotubes. EP 0205 556 A 1 (Hyperion Catalysis International) describes such carbon nanotubes which are produced by means of an iron-containing catalyst and the reaction of various hydrocarbons at high temperatures above 800 to 1000° C. Shaikhutdinov et al. (Shamil' K. Shaikhutdinov, L. B. Avdeeva, O. V. Goncharova, D. I. Kochubey, B. N. Novgorodov, L. M. Plyasova, "Coprecipitated Ni—Al and Ni—Cu—Al catalysts for methane decomposition and carbon deposition I.", Applied Catalysis A: General, 126, 1995, pages 125-139) mention Ni-based systems as being active in the decomposition of methane to carbon nanomaterials.

In CA 2374848 (Centre National de la Recherche Scientifique, FR) there is disclosed as a possible process for the mass production of carbon nanotubes a process in which a yield of 3 g of CNTs/g of catalyst is achieved using acetylene as carbon donor on a cobalt catalyst. This comparatively very low yield makes the process appear uncritical with regard to ensuring thorough mixing but requires expensive purification steps to obtain a product suitable for use.

Mauron et al. (Ph. Mauron, Ch. Emmenegger, P. Sudan, P. Wenger, S. Rentsch, A. Züttel, "Fluidised-bed CVD synthesis of carbon nanotubes on $Fe_2O_3$/MgO", Diamond and Related Materials 12 (2003) 780-785) also achieve only very low yields (max. 0.35 g of CNTs/g of catalyst) in the production of CNTs from isopentane or acetylene on an iron catalyst. For that reason they also do not discuss possible difficulties during thorough mixing in the reactor during the growth process of the agglomerates.

EP 1399384 (Institut National Polytechnique, Toulouse, FR) describes the production of carbon nanotubes in a CCVD process with an upstream reactor for in-line catalyst production, wherein the catalyst can have a mean particle size of from 10 μm to 1000 μm and can reach a volume increase of the agglomerates of up to twenty times the catalyst amount. With regard to fluidization, it is merely required that the superficial gas velocity in the reactor remains above the minimum fluidization velocity of the particle collective in the reactor and below the gas velocity required for the formation of a plug flow.

In a dissertation by Nijkamp (Utrecht University/NL, 2002, "Hydrogen Storage using Physisorption Modified Carbon Nanofibers and Related Materials"), the production of carbon nanotubes by means of nickel-containing catalysts and methane as carbon donor is described. However, only the laboratory scale is considered therein (reactor inside diameter 25 mm) and, with a relatively low yield (27 g of CNTs/g of catalyst) overall, only a very small amount of material (10-30 g) is produced. The material so produced must be purified before it is used further because the catalyst residues have a disruptive effect in most applications and nickel must not pass into the end products owing to its carcinogenic action.

In the various processes using different catalyst systems that have been mentioned hereinbefore, carbon nanotubes having different structures are produced, and they can be removed from the process predominantly in the form of carbon nanotube powder.

Conventional structures of such tubes are those of the cylinder type. In the case of cylindrical structures, a distinction is made between single-wall monocarbon nanotubes and multi-wall cylindrical carbon nanotubes. Conventional processes for their production are, for example, arc discharge, laser ablation, chemical vapor deposition (CVD process) and catalytic chemical vapor deposition (CCVD process).

Such cylindrical carbon nanotubes can also be prepared by an arc discharge process. Iijima, Nature 354, 1991, 56-58 reports on the formation, by the arc discharge process, of carbon tubes consisting of two or more graphene layers which are rolled up to form a seamless closed cylinder and are nested inside one another. Chiral and achiral arrangements of the carbon atoms along the longitudinal axis of the carbon fibers are possible depending on the rolling vector.

WO 86/03455A1 describes the production of carbon filaments which have a cylindrical structure with a constant diameter of from 3.5 to 70 nm, an aspect ratio (ratio of length to diameter) of greater than 100 and a core region. These fibrils consist of a large number of interconnected layers of ordered carbon atoms, which are arranged concentrically around the cylindrical axis of the fibrils. These cylinder-like nanotubes were produced by a CVD process from carbon-containing compounds by means of a metal-containing particle at a temperature of from 850° C. to 1200° C.

A process for the production of a catalyst which is suitable for the production of conventional carbon nanotubes having a cylindrical structure has also become known from WO2007/093337A2. When this catalyst is used in a fixed bed, relatively high yields of cylindrical carbon nanotubes having a diameter in the range from 5 to 30 nm are obtained.

A completely different way of producing cylindrical carbon nanotubes has been described by Oberlin, Endo and Koyam (Carbon 14, 1976, 133). Aromatic hydrocarbons, for example benzene, are thereby reacted on a metal catalyst. The resulting carbon tube exhibits a well-defined, graphitic hollow core which has approximately the diameter of the catalyst particle, on which there is further, less graphitically ordered carbon. The authors suppose that the graphitic core is formed first by rapid catalytic growth, and then further carbon is deposited pyrolitically. The entire tube can be graphitized by treatment at high temperature (2500° C.-3000° C.).

Most of the above-mentioned processes (arc discharge, spray pyrolysis or CVD) are used today for the production of carbon nanotubes. The production of single-wall cylindrical carbon nanotubes is very expensive in terms of apparatus, however, and proceeds according to the known processes with a very low formation rate and often also with many secondary reactions, which result in a high proportion of undesirable impurities, that is to say the yield of such processes is comparatively low. For this reason, the production of such carbon nanotubes is still extremely expensive even today, and they are used in small amounts only for highly specialized applications.

As early as 1960, Bacon et al., J. Appl. Phys. 34, 1960, 283-290 described the existence of carbon whiskers, which consist of a rolled-up graphene layer. The structure is referred to as scroll type. The production process described by Bacon is based on the evaporation of a carbon electrode in an arc (arc discharge).

Similar structures of carbon tubes, in which a cohesive graphene layer (so-called scroll type) or a broken graphene layer (so-called onion type) is the basis for the structure of the nanotube, were later also found by Zhou et al., Science, 263, 1994, 1744-1747 and by Lavin et al., Carbon 40, 2002, 1123-1130. These carbon nanotubes are present in a carbon black produced by the arc discharge process in admixture with many other carbon structures. Such scroll-type or onion-type carbon nanotubes cannot readily be separated or produced in pure form. Industrial production of such special forms does not therefore come into consideration.

Carbon nanotubes consisting of a single rolled-up graphene layer were later also produced by means of a pyrolysis process by Ruland et al., Carbon 41, 2003, 423-427. Dravid et al., Science 259, 1993, 1601-1604 and Feng et al., J. Phys. Chem. Solids, 58, 1997, 1887-1892 describe intermediate structures in which graphene layers are wound round a single thicker carbon nanotube of the so-called bucky type. Bucky type is a name for multi-wall carbon nanotubes with round closed ends of graphite, which have concentric closed graphite cylinders.

In all these processes for the production of scroll- or onion-type carbon tubes, the energy outlay is very high and the yield is low, which makes practicable or industrial production impossible.

The production of multi-wall carbon nanotubes in the form of seamless cylindrical nanotubes nested inside one another is today carried out commercially in relatively large amounts predominantly using catalytic processes. These processes conventionally exhibit a higher yield than the above-mentioned arc discharge process and other processes, and are today typically carried out on the kg scale (several hundred kilos/day worldwide). The MW carbon nanotubes so produced are generally somewhat less expensive than single-wall nanotubes and are therefore used in certain amounts as a performance-enhancing additive in other materials.

The object of the present invention is to develop a process for producing carbon nanotubes in even greater amounts, which exhibit at least the properties of the known MWCNT structures.

Furthermore, the CNT material is to have high purity in respect of metallic impurities and amorphous carbon, impurities which can lead to impairment of material properties on incorporation into matrix materials, for example into polymers. Furthermore, the product is to have in particular good pourability and especially is to be largely free of dust and is to have as high a bulk density of the CNTs as possible, in order to facilitate transport and handling both during production and during the filling of the CNT material into containers and its transfer into different containers, and during subsequent incorporation. A large inner surface area of the CNT material would also be particularly advantageous.

It was possible to achieve this object by the provision of a chosen catalytic gas-phase process by means of which, by the choice of special suitable catalysts and process conditions, novel carbon nanotube powders are formed which consist predominantly of carbon nanotubes consisting of one or more continuous graphite layers which are rolled up to form a tubular structure.

SUMMARY OF THE INVENTION

The invention accordingly provides a carbon nanotube powder containing carbon nanotubes, characterized in that the carbon nanotubes comprise or, preferably, consist substantially of one or more graphite layers, wherein the graphite layers are composed of two or more graphene layers arranged one above the other, and the graphite layers form a rolled-up structure, in that the carbon nanotubes, in cross-section, exhibit a spiral arrangement of the graphite layers, wherein the mean diameter of the carbon nanotubes is from 3 to 100 nm, preferably from 4 to 75 nm, particularly preferably from 5 to 30 nm.

In contrast to the previous CNTs described in the literature, with structures of the scroll type having only one continuous or broken graphene layer, in the novel structural forms of carbon a plurality of graphene layers are combined to form a pile, which is in rolled-up form (multi-scroll type). The carbon nanotubes according to the invention can accordingly be regarded as a further form of carbon and are comparable in terms of structure to the known carbon nanotubes of the simple scroll type, such as multi-wall cylindrical monocarbon nanotubes (cylindrical MWCNTs) to single-wall cylindrical carbon nanotubes (cylindrical SWCNTs).

Unlike in the onion-type structures still described occasionally in the prior art, the individual graphene or graphite layers in the novel carbon nanotubes evidently run, when viewed in cross-section, continuously from the centre of the CNTs to the outside edge, without interruption, as is shown by initial investigations. This can permit, for example, improved and more rapid intercalation of other materials, such as lithium, potassium, rubidium metal or iron chloride, in the tube structure, because more open edges are available as entry zones of the intercalates, as compared with CNTs having a simple scroll structure (Carbon 34, 1996, 1301-1303) or CNTs having an onion-type scroll structure (Science 263, 1994, 1744-1747).

The carbon nanotubes are present in the carbon nanotube powder typically in particular in the form of agglomerates of long fibers.

DETAILED DESCRIPTION

Preference is given to a carbon nanotube powder containing carbon nanotubes, in which the length-to-diameter ratio of the carbon nanotubes is at least 5, in particular at least 30, particularly preferably at least 50.

A major advantage of the carbon nanotube powder according to the invention is that it is largely free of dust and has good pourability as well as a high bulk density while at the same time having a large inner surface area. These ensure that the novel carbon nanotube powder can be handled without problems during application of the material and its incorporation into other materials, for example plastics. The novel multi-scroll carbon nanotubes, which, owing to their structure, are evidently readily amenable to chemical functionalization at the outer free sides of the graphene layers, permit improved binding to the matrix material in question when used, for example, as a polymer additive.

In such novel carbon nanotubes, markedly more reactive carbon atoms, for example, are available at the outer edges along the axis of the carbon nanotubes than in known mono-scroll tubes or cylinder-like carbon tubes. As a result, more functional groups can in principle be applied, and in addition they can be applied more easily, than in other carbon nanotubes, which is important, for example, for improved binding of the tubes via those groups into polymers, for better stabilization of the tubes in solvents or for loading with pharmaceutical active ingredients or active catalyst components. In contrast in particular to cylindrical carbon nanotubes which, when viewed in cross-section, have circular closed graphene layers, the actual structure of the novel tubes is not influenced or is influenced only slightly in the chemical functionalization, so that the electrical properties are retained to the greatest possible extent or are not or are only minimally impaired.

Preference is given to a carbon nanotube powder which is characterized in that the content of impurities in the powder, in particular of metals or metal compounds, particularly preferably of metal oxides, is not more than 7 wt. %, preferably not more than 5 wt. %.

The impurities include in particular metals or metal compounds of the transition metals, in particular of sub-groups VII and VIII of the Periodic Table of the elements, or of the alkali metals or alkaline earth metals or silicon or silicon oxide, and particularly preferably metals or metal compounds selected from the group aluminium, magnesium, titanium, zirconium, sodium, calcium, iron, nickel, manganese, molybdenum and cobalt. In uses of the CNTs relating to electronic (semi-conductor) components or fuel cells or batteries, the presence of foreign metals is generally undesirable. Some of the above-mentioned metals are additionally regarded as being toxicologically harmful and, as outlined at the beginning, are to be found in various CNTs known from the prior art as a result of the production. When the CNTs are used as an additive for polymers, the presence of certain metals (e.g. iron in polycarbonate) is likewise undesirable, because they catalytically accelerate the decomposition of the polymers under some circumstances and reduce the lifetime of corresponding composites. This disadvantage is avoided with the particular novel carbon nanotube powder.

The content of pyrolytically deposited carbon in the carbon nanotube powder is preferably not more than 7 wt. %, particularly preferably not more than 2 wt. %, very particularly preferably not more than 1 wt. %. Pyrolytically deposited carbon is present predominantly in the form of amorphous carbon, does not have a crystal structure or has a structure which is not comparable with the typical ordered graphitic crystal structure of pure CNTs. Pyrolytically deposited carbon optionally contains impurities of higher, polynuclear aromatic compounds which are technically and ecologically undesirable and would have to be separated expensively from the pure fibers based on a graphite structure in order not to adversely affect the material properties of composites produced from CNTs.

In a preferred embodiment of the invention, the carbon nanotube powder is in the form of an agglomerate, wherein at least 95 wt. % of the agglomerate particles have an outside diameter in the range from 5 µm to 10,000 µm, preferably from 30 µm to 5000 µm, particularly preferably from 50 µm to 3000 µm. This ensures good flowability or pourability of the CNT powder, so that handling of the product during metering, transfer, storage and other process steps in the production, storage, processing, incorporation and other processing steps relevant for the product is substantially simplified. At the same time, the dust-forming behavior is greatly reduced. This simplifies technical and organizational measures for minimizing the dust load in the workplace and minimizes pollution of the workplace.

The carbon nanotube powder preferably contains more than 50%, particularly preferably at least 90%, very particularly preferably at least 95%, of the above-described novel carbon nanotubes with roll-like graphene layers.

Preference is given also to a carbon nanotube powder which is characterized in that the bulk density (according to EN ISO 60) of the carbon nanotube powder is from 20 to 450 kg/m$^3$, preferably from 80 to 350 kg/m$^3$, very particularly preferably from 110 to 250 kg/m$^3$. These agglomerate properties of a comparatively high bulk density for carbon nanotube powders contribute substantially to a large degree of freedom from dust and good handling as well as space-saving and hence economically transportable packaging. In addition, the pourability or flowability is positively influenced because the density, in addition to other properties such as, for example, particle shape and particle geometry, has a fundamental influence on this parameter.

Particular preference is given to a carbon nanotube powder which is characterized in that the specific surface area (nitrogen adsorption according to BET) is from 20 to 1500 m$^2$/g, preferably from 30 to 800 m$^2$/g, particularly preferably from 90 to 600 m$^2$/g. A large surface area permits good adhesion of the carbon nanotubes, for example in a polymer composite, as a result of which better mechanical properties can be achieved. At the same time, however, the viscosity of the composite increases considerably. The above-indicated optimum BET range is given taking into consideration the processes for incorporating the carbon nanotube powder or carbon nanotubes into materials such as polymers (e.g. by using an extruder) and the required concentration of carbon nanotubes.

Particular preference is given also to a carbon nanotube powder in which the carbon nanotubes, when viewed in cross-section, have a maximum outside diameter of up to 500 nm, preferably up to 100 nm, particularly preferably up to 50 nm, and hence form very uniform carbon nanotube powders having a narrow diameter distribution of the carbon nanotubes contained therein.

The carbon nanotube powder according to the invention is obtainable by a special catalytic gas-phase process under defined process conditions and with the use of chosen catalysts. Surprisingly, when a fluidized bed is used instead of a fixed bed in conjunction with chosen catalysts for the production of carbon nanotubes based on manganese and cobalt, and when a comparatively short residence time of the catalyst and the carbon nanotubes in the fluidized bed is used, a carbon nanotube powder is obtained which contains carbon nanotubes having a novel original structure and also has the described advantages in terms of processing.

The invention further provides a process for the production of a carbon nanotube powder, characterized in that $C_1$-$C_3$-hydrocarbons are decomposed on a heterogeneous catalyst at a temperature of from 500 to 1000°, preferably from 600 to 800° C., in a reactor with a moving bed, wherein the mean residence time of the catalyst in the reaction zone is not more than one hour. The catalyst used is a transition metal catalyst based on Co and Mn, in particular mixed oxides thereof, wherein the proportion of Co is preferably from 40 to 60 mol % and the proportion of Mn is preferably from 60 to 40 mol %, based on the sum of Co and Mn. There are suitable as the hydrocarbon preferably ethene or propene, which are supplied to the process individually or in the form of a mixture also together with inert gases (e.g. nitrogen or noble gases). The mean residence time of the catalyst in the reaction zone is preferably from 20 to 45 minutes, particularly preferably from 25 to 35 minutes.

The process is particularly preferably carried out using ethene. The process can be carried out continuously, semi-continuously or discontinuously, preferably continuously.

In a preferred embodiment, the catalyst to be used is prepared from water-soluble salts in an aqueous medium by means of lyes in a coprecipitation of the catalytically active metal compounds Co and Mn together with at least one further component which forms either an intermediate binder material or a catalytically active mixed compound in further steps of the catalyst treatment. Examples of such further components which may be mentioned include Al, Mg, Si, Zr, Ti, etc. or conventional mixed metal oxide-forming elements known to the person skilled in the art. The precipitation is effected in particular by addition of alkaline solutions, in particular of alkaline lye, to the metal salt solution. The content of further components can be up to 80 wt. %, based on the total catalyst composition. The catalysts preferably have a content of further components of from 5 to 75 wt. %.

The catalyst, which is obtained in the form of a solid, can be separated from the starting material solutions by methods known to the person skilled in the art, such as, for example, filtration, centrifugation, concentration by evaporation and concentration. Centrifugation and filtration are preferred. The resulting solid can be further washed or can be used further directly, as obtained. For improved handleability of the resulting catalyst, it is preferably dried and ground. As is known with heterogeneous catalysts, further conditioning of the catalysts can be advantageous. This conditioning can be calcination and thermal treatment as well as treatment with reactive atmospheres or, for example, steam, with the aim of improving the catalytic properties. This is achieved, for example, by thermal pre-treatment in an oxidizing atmosphere at temperatures of from 300° C. to 900° C.

The conditioning can additionally be preceded or followed by shaping and/or screening. Thereafter, the catalyst can be used directly. The catalyst is preferably used for carrying out the novel process with a particle size in the range from 30 to 100 µm, particularly preferably from 40 to 80 µm. Fluidization in the fluidized bed and the yield of carbon nanotube powder is thereby improved.

The catalyst that is particularly preferably to be used in the process according to the invention contains from 45 to 55 mol % Mn and from 55 to 45 mol % Co, based on the content of active components in metallic form.

The process according to the invention can be carried out in different types of fluidized bed reactor with thorough mixing of the reactor contents. Examples which may be mentioned here are in particular reactors having a bubble-forming, turbulent or irradiated fluidized bed, or an internally or externally circulating fluidized bed. Particular preference is given to the use of a bubble-forming fluidized bed. It is also possible to introduce the catalyst into a fluidized bed reactor filled with particles.

These particles can be inert particles and/or can consist wholly or partially of a further catalytically active material. These particles can also be agglomerates of carbon nanotubes.

The process can be carried out, for example, continuously or discontinuously, continuously or discontinuously relating both to the supply of the catalyst and to the discharge of the carbon nanotubes that have been formed with the consumed catalyst.

There come into consideration as starting material gases hydrocarbons from the group: methane, ethane, propane, ethene and propene. Mixtures of the above-mentioned hydrocarbons can also be used.

The invention also provides carbon nanotubes, characterized in that the carbon nanotubes comprise or, preferably, consist substantially of one or more graphite layers, wherein the graphite layers are composed of two or more graphene layers arranged one above the other, and the graphite layers form a rolled-up structure, in that the carbon nanotubes, in cross-section, exhibit a spiral arrangement of the graphite layers, wherein the mean diameter of the carbon nanotubes is from 3 to 100 nm, preferably from 4 to 75 nm, particularly preferably from 5 to 30 nm.

The length-to-diameter ratio of the carbon nanotubes is in particular at least 5, preferably at least 10, particularly preferably at least 20, very particularly preferably at least 50.

The content of impurities in the carbon nanotubes, in particular of metals or metal compounds, particularly preferably of metal oxides, is not more than 7 wt. %, preferably not more than 5 wt. %.

The impurities include in particular metals or metal compounds of the transition metals, in particular of sub-groups VII and VIII of the Periodic Table of the elements, or of the alkali metals or alkaline earth metals or silicon or silicon oxide, and in particular metals or metal compounds selected from the group aluminium, magnesium, titanium, zirconium, sodium, calcium, iron, nickel, manganese, molybdenum and cobalt.

The content of pyrolytically deposited carbon in the carbon nanotubes is preferably not more than 7 wt. %, particularly preferably not more than 2 wt. %, very particularly preferably not more than 1 wt. %.

In a preferred embodiment, the novel carbon nanotubes, when viewed in cross-section, have a maximum outside diameter of up to 500 nm, preferably from 10 to 100 nm, particularly preferably from 15 to 50 nm. The minimum diameter is typically about 3 nm.

The novel carbon nanotubes are obtainable, for example, from the carbon nanotube powders according to the invention by grinding and dispersion processes known per se. There can be used for this purpose, for example, all types of mills, dissolvers and dispersers, in particular those which permit high pressures and shear rates for high energy inputs, also ultrasonic emitters, roll mills, calanders, single- and multi-shaft screw extruders, to mention only a few.

The invention therefore also provides a process for the production of the novel carbon nanotubes by deagglomeration of the carbon nanotube powders according to the invention, in particular by grinding or dispersion with the introduction of energy, which is necessary to break the carbon nanotube powders into individual carbon nanotubes.

Because the separated carbon nanotubes have a pronounced tendency to agglomeration, the deagglomeration is preferably carried out in a stabilizing matrix of, for example, a polymer that is still liquid in itself or that has been liquefied.

The invention further provides the use of the novel carbon nanotube powders or of the carbon nanotubes as an additive in other known matrix materials, for example for polymers, rubbers, adhesives, coating compositions, thickening compositions, ceramics, metals, metal alloys, glasses, concrete and other building materials, textiles and composite materials, or as an adsorber in particular for volatile compounds, for example for gases or for biological compounds, for example for enzymes.

The invention further provides the use of the novel carbon nanotube powders or of the carbon nanotubes as a constituent of gas storage materials, in particular for the storage of hydrogen.

The invention further provides the use of the novel carbon nanotube powders or of the carbon nanotubes as a conductive additive or as an active or surface-area-increasing component in electrodes, in solar cells, actuators, sensors, inks or pastes, as well as in energy storage means, in particular in batteries, capacitors (supercaps), fuel cells or accumulators.

The invention further provides the use of the novel carbon nanotube powders or of the carbon nanotubes as a substrate for catalysts.

The invention also provides the use of the novel carbon nanotube powders or of the carbon nanotubes as a substrate for pharmaceutical active ingredients or for active ingredients for crop protection.

BRIEF DESCRIPTION OF THE DRAWINGS

The invention is explained in greater detail hereinbelow, by way of example, with reference to the figures.

Figure 1:
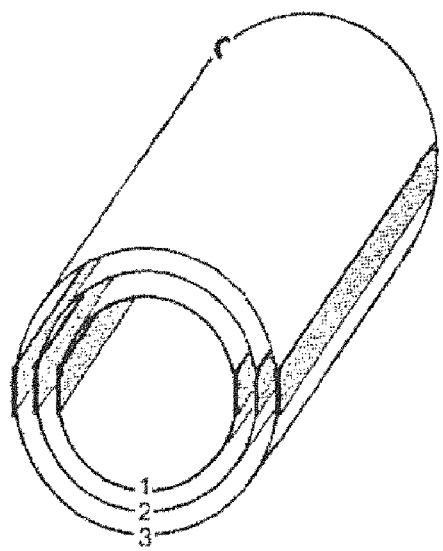
FIGS. 1 to 3 show, in diagrammatic form, various known structures of carbon tubes.
Figure 2:
Figure 3:
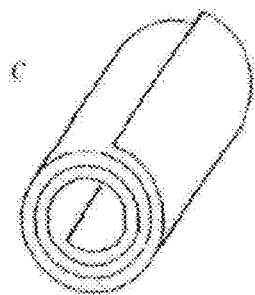
Figure 4:
FIGS. 4 and 5 show views of the carbon nanotubes according to the invention.
Figure 5:

In detail,

FIG. 1 shows multi-wall cylindrical carbon tubes (according to Iijima, Nature 354, 56-58, 1991), FIG. 2 shows carbon tubes with a scroll-type structure according to Bacon (J. Appl. Phys. 34, 1960, 283-290), FIG. 3 shows the simple form of the carbon tubes with a scroll-type structure according to Iijima (Nature 354, 56-58, 1991), FIG. 4 shows, in diagrammatic form, the structure of the carbon nanotubes according to the invention in cross-section, FIG. 5 shows the cross-section of a carbon nanotube according to the invention as a transmission electron microscope photograph.

EXAMPLES

Example 1

Preparation of the Catalyst

A solution of 0.306 kg of $Mg(NO_3)_2 \cdot 6H_2O$ in water (0.35 liter) was mixed with a solution of 0.36 kg of $Al(NO_3)_3 \cdot 9H_2O$ in 0.35 liter of water. Then 0.17 kg of $Mn(NO_3)_2 \cdot 4H_2O$ and 0.194 kg of $Co(NO_3)_2 \cdot 6H_2O$, each dissolved in 0.5 liter of water, were added and the entire mixture was brought to a pH value of about 2 by the addition of nitric acid, while stirring for 30 minutes. A stream of this solution was mixed in a mixer with 20.6 wt. % sodium hydroxide solution in a ratio of 1.9:1, and the resulting suspension was introduced into a receiver containing 5 liters of water. The pH value of the receiver was maintained at about 10 by controlling the sodium hydroxide addition.

The precipitated solid was separated from the suspension and washed several times. The washed solid was then dried in the course of 16 hours in a paddle drier, the temperature of the drier being increased from room temperature to 160° C. in the course of the first eight hours. The solid was then ground in a laboratory mill to a mean particle size of 50 μm, and the middle fraction in the range from 30 μm to 100 μm particle size was removed in order to facilitate the subsequent calcination, especially to improve the fluidization in the fluidized bed and achieve a high yield of product. The solid was then calcined for 12 hours in a 500° C. oven, with admission of air, and then cooled for a period of 24 hours. The catalyst material was then allowed to stand for 7 days at room temperature for after-oxidation. A total of 121.3 g of catalyst material was isolated.

Example 2

Production of the CNTs in a Fluidized Bed

The catalyst prepared in Example 1 was tested in a fluidized bed apparatus on a laboratory scale. To this end, a given amount of catalyst was placed in a steel reactor having an inside diameter of 100 mm, which was heated from the outside by a heat transfer medium. The temperature of the fluidized bed was regulated by PID control of the electrically heated heat transfer medium. The temperature of the fluidized bed was determined by a thermal element. Starting material gases and inert diluent gases were passed into the reactor via electronically controlled mass flow regulators.

The reactor was first rendered inert with nitrogen and heated to a temperature of 650° C. An amount of 24 g of catalyst 1 according to Example 1 was then metered in.

Immediately thereafter, the starting material gas, as a mixture of ethene and nitrogen, was switched on. The volume ratio of the starting material gas mixture was ethene:$N_2$=90:10. The total volume flow was adjusted to 40 LN·$min^{-1}$. The catalyst was exposed to the starting material gases for a period of 33 minutes. The continuing reaction was then stopped by interrupting the supply of starting material, and the contents of the reactor were removed.

The amount of deposited carbon was determined by weighing, and the structure and morphology of the deposited carbon were determined by means of REM and TEM analyses. The amount of deposited carbon relative to catalyst used, referred to hereinbelow as the yield, was defined on the basis of the mass of catalyst after calcination (mCat,0) and the increase in weight after reaction (mTotal−mCat,0): Yield=(mTotal−mCat,0)/mCat,0.

The evaluation showed a catalyst yield, averaged over 5 test runs, of 35.3 g of carbon nanotube powder per g of catalyst used. The TEM photographs showed structures of about 2 to 3 rolled-up graphite layers each consisting of from 8 to 12 graphene layers. The carbon fibers had a mean diameter of 16 nm. The length-to-diameter ratio was at least 100.

Testing of the purity by ignition loss gave a content of 96.9% carbon.

No pyrolytically deposited carbon was discernible in the carbon nanotube powders on the TEM photographs.

The carbon nanotube powder had a surface area, measured according to BET, of 260 $m^2$/g.

The bulk density of the agglomerate, averaged over 5 test runs, was 152 kg/$m^3$.

Example 3

Separation of the Carbon Nanotubes

Owing to the large surface area of the carbon nanotubes, separation is expedient only in combination with stabilization (immobilization in a matrix, addition of substances acting as stabilizer) of the separation state, because rapid reagglomeration of the carbon nanotubes otherwise occurs because of the high van der Waals forces.

The carbon nanotube powder produced in Example 2 was introduced together with polycarbonate (Makrolon 2805) into the main intake of a co-rotating twin-screw extruder (ZSK 26Mc, L/D 36). The temperature of the extruder was 280° C. The throughput was adjusted to 26 kg/h composite. The speed was adjusted to 400 rpm. The mass ratio of the carbon nanotube powder to polycarbonate was 5:95. The strand emerging from the extruder was cooled in a water-bath and then granulated. A TEM photograph of a section prepared from the composite shows the carbon nanotubes present separately in the polycarbonate.

What is claimed is:

1. A powder comprising carbon nanotubes, wherein the carbon nanotubes comprise one or more graphite layers, wherein the graphite layers are composed of two or more graphene layers arranged one on top of the other, and the graphite layers form a rolled-up structure, wherein the carbon nanotubes, in cross-section, exhibit a spiral arrangement of the graphite layers running from the center of the carbon nanotubes to the outside edges, without interruption, and wherein the carbon nanotubes exhibit a mean diameter of from 3 to 100 nm, said powder being in the form of an agglomerate of particles, wherein at least 95wt.% of the agglomerate particles have an outside diameter in the range from 5 µm to 10,000 µm.

2. Carbon nanotube powder according to claim 1, wherein the carbon nanotubes exhibit a length-to-diameter ratio of at least 5.

3. Carbon nanotube powder according to claim 1, which has a content of impurities of not more than 7wt.%.

4. Carbon nanotube powder according to claim 3, wherein the impurities comprise metals or metal compounds of transition metals, or of alkali metals or alkaline earth metals or silicon or silicon oxide.

5. Carbon nanotube powder according to claim 1, which has a content of pyrolytically deposited carbon of not more than 7wt.%.

6. Carbon nanotube powder according to claim 1, which has a bulk density (according to EN ISO 60) of from 20 to 450 kg/$m^3$.

7. Carbon nanotube powder according to claim 1, which has a specific surface area (nitrogen adsorption according to BET) of from 20 to 1500 $m^2$/g.

8. Carbon nanotube powder according to claim 1, wherein the carbon nanotubes, when viewed in cross-section, have a maximum outside diameter of up to 500 nm.

9. Carbon nanotubes comprising one or more graphite layers, wherein the graphite layers are composed of two or more graphene layers arranged one above the other, and the graphite layers form a rolled-up structure, wherein the carbon nanotubes, in cross-section, exhibit a spiral arrangement of the graphite layers running from the center of the carbon nanotubes to the outside edges, without interruption, and wherein the carbon nanotubes exhibit a mean diameter of from 3 to 100 nm.

10. Carbon nanotubes according to claim 9, which exhibit a length-to-diameter ratio of at least 5.

11. Carbon nanotubes according to claim 9, which have a content of impurities of not more than 7wt.%.

12. Carbon nanotubes according to claim 11, wherein the impurities comprise metals or metal compounds of transition metals, or of alkali metals or alkaline earth metals or silicon or silicon oxide.

13. Carbon nanotubes according to claim 9, which have a content of pyrolytically deposited carbon of not more than 7wt.%.

14. Carbon nanotubes according to claim 9, which, when viewed in cross-section, have a maximum outside diameter of up to 500 nm.

* * * * *